US010421961B2

(12) United States Patent
Brodie et al.

(10) Patent No.: US 10,421,961 B2
(45) Date of Patent: Sep. 24, 2019

(54) METHODS, SYSTEMS, AND COMPOSITIONS FOR NEURONAL DIFFERENTIATION OF MULTIPOTENT STROMAL CELLS

(75) Inventors: Chaya Brodie, Southfield, MI (US); Shimon Slavin, Tel-Aviv (IL)

(73) Assignee: EXOSTEM BIOTEC LTD, Tel-Aviv (IL)

( * ) Notice: Subject to any disclaimer, the term of this patent is extended or adjusted under 35 U.S.C. 154(b) by 0 days.

(21) Appl. No.: 13/377,558

(22) PCT Filed: Jun. 10, 2010

(86) PCT No.: PCT/US2010/038168
§ 371 (c)(1),
(2), (4) Date: Feb. 23, 2012

(87) PCT Pub. No.: WO2010/144698
PCT Pub. Date: Dec. 16, 2010

(65) Prior Publication Data
US 2012/0148550 A1    Jun. 14, 2012

Related U.S. Application Data

(60) Provisional application No. 61/185,773, filed on Jun. 10, 2009.

(51) Int. Cl.
*C12N 15/113* (2010.01)
*C12N 5/0793* (2010.01)
*A61K 31/7105* (2006.01)

(52) U.S. Cl.
CPC ........ *C12N 15/113* (2013.01); *A61K 31/7105* (2013.01); *C12N 5/0619* (2013.01); *C12N 2310/141* (2013.01); *C12N 2330/10* (2013.01); *C12N 2501/13* (2013.01); *C12N 2501/65* (2013.01); *C12N 2506/1353* (2013.01); *C12N 2510/00* (2013.01)

(58) Field of Classification Search
None
See application file for complete search history.

(56) References Cited

U.S. PATENT DOCUMENTS

| 7,250,294 B2 * | 7/2007 | Carpenter et al. ............ 435/377 |
| 2006/0166362 A1 * | 7/2006 | Dezawa ............... C12N 5/0619 435/455 |
| 2008/0138319 A1 * | 6/2008 | Deng et al. .................. 424/93.2 |
| 2008/0171715 A1 | 7/2008 | Brown et al. |
| 2008/0241207 A1 | 10/2008 | Tang et al. |

FOREIGN PATENT DOCUMENTS

| WO | WO 2008/053909 | 5/2008 |
| WO | WO 2010/144698 | 12/2010 |

OTHER PUBLICATIONS

Papagiannakopoulos et al., MicroRNAs: regulators of oncogenesis and stemness, BMC Medicine, 2008, 6: 15 (Open Access version available online at http://www.biomedcentral.com/content/pdf/1741-7015-6-15.pdf).*

Schwartz et al. Differentiation of Neural Lineage Cells From Human Pluripotent Stem Cells. Methods, 2008. 45:142-158.*
Silber et al. MiR-124 and MiR-137 Inhibit Proliferation of Glioblastoma Multiforme Cells and Induce Differentiation of Brain Tumor Stem Cells. BMC Medicine, 2008. 6(14): 17 pages.*
International Search Report and the Written Opinion dated Dec. 2, 2011 From the International Searching Authority Re. Application No. PCT/US2010/038168.
Invitation to Pay Additional Fees dated Sep. 30, 2010 From the International Searching Authority Re. Application No. PCT/US2010/038168.
Krichevsky et al. "Specific MicroRNAs Modulate Embryonic Stem Cell-Derived Neurogenesis", Stem Cells, 24(4): 857-864, Apr. 2006.
Lakshmipathy et al. "Concise Review. Micro RNA Expression in Multipotent Mesenchymal Stromal Cells", Stem Cells, 26(2): 356-363, Feb. 2008.
Makeyev et al. "The MicroRNA MiR-124 Promotes Neuronal Differentiation by Triggering Brain-Specific Alternative Pre-mRNA Splicing", Molecular Cell, 27: 435-448, Aug. 3, 2007.
International Preliminary Report on Patentability dated Dec. 22, 2011 From the Intemaional Bureau of WIPO Re. Application No. PCT/US2010/038168.
Translation of Notification of Office Action dated Feb. 17, 2013 From the State Intellectual Property Office of the People's Republic of China Re. Application No. 201080035364.3.
Translation of Search Report dated Feb. 17, 2013 From the State Intellectual Property Office of the People's Republic of China Re. Application No. 201080035364.3.
Completion Requirement Letter dated Jan. 15, 2014 From the Canadian Intellectual Property Office Re. Application No. 2,772,869.
Communication Pursuant to Rules 70(2) and 70a(2) EPC dated Aug. 16, 2013 From the European Patent Office Re. Application No. 10786843.2.
Supplementary European Search Report and the European Search Opinion dated Jul. 29, 2013 From the European Patent Office Re. Application No. 10786843.2.
Packer et al. "The Bifunctional MicroRNA MiR-9/MiR-9* Regulates REST and CoREST and Is Downregulated in Huntington's Disease", The Journal of Neuroscience, XP055071508, 28(53): 14341-14346, Dec. 31, 2008.

(Continued)

*Primary Examiner* — Christopher M Babic
*Assistant Examiner* — Kimberly A. Aron
(74) *Attorney, Agent, or Firm* — The Roy Gross Law Firm, LLC; Roy Gross

(57) ABSTRACT

Some embodiments of the invention comprise methods, systems, and compositions to selectively induce, whether in vitro or in vivo, the neuronal differentiation of multipotent stromal cells through the application of microRNAs, including but not limited to miRNA-124, miRNA-137 and/or miRNA-9* expression products of those miRNAs, and molecules and compositions containing functional elements of those miRNAs. Some embodiments of the invention also comprise the therapeutic administration and use of such induced cells to treat mammalian injuries and diseases, including but not limited to, nervous system injuries or diseases that may otherwise result in decreased cell or system function.

6 Claims, 4 Drawing Sheets
Specification includes a Sequence Listing.

(56) References Cited

OTHER PUBLICATIONS

Yoo et al. "MicroRNA-Mediated Conversion of Human Fibroblasts to Neurons", Nature, XP002702842, 476(7359): 228-231, Aug. 11, 2011.
Notice of Reason for Rejection dated Jul. 4, 2014 From the Japanese Patent Office Re. Application No. 2012-515138 and Its Translation Into English.
Castillo et al. "Immunostimulatory Effects of Mesenchymal Stem Cell-Derived Neurons: Implications for Stem Cell Therapy in Allogeneic Transplantations", Clinical and Translational Science, 1(1): 27-34, May 2008.
Schoolmeesters et al. "Functional Profiling Reveals Critical Role for MiRNA in Differentiation of Human Mesenchymal Stem Cells", PLoS One, 4(5): e5605-1-e5605-9, May 2009.
Silber et al. "MiR-124 and MiR-137 Inhibit Proliferation of Glioblastoma Multiforme Cells and Induce Differentiation of Brain Tumor Stem Cells", BMC Medicine, 6(14): 1-17, Jun. 24, 2008.
Office Action dated Mar. 13, 2014 From the Israel Patent Office Re. Application No. 216871 and Its Translation Into English.
Office Action dated May 27, 2015 From the Israel Patent Office Re. Application No. 216871 and Its Translation Into English.
Examination Report dated Jun. 10, 2015 From the Instituto Mexicano de la Propiedad Industrial Re. Application No. MX/a/2011/013337 and Its Translation Into English.
Notice of Reason for Rejection dated Apr. 16, 2015 From the Japanese Patent Office Re. Application No. 2012-515138 and Its Machine Translation in English.

\* cited by examiner (y-axis = beta III tubulin mRNA/S12 mRNA)

SEQUENCE LISTING

```
<160> NUMBER OF SEQ ID NOS: 11

<210> SEQ ID NO 1
<211> LENGTH: 20
<212> TYPE: RNA
<213> ORGANISM: Homo sapiens

<400> SEQUENCE: 1
uaaggcacgc ggugaaugcc                                              20

<210> SEQ ID NO 2
<211> LENGTH: 23
<212> TYPE: RNA
<213> ORGANISM: Homo sapiens

<400> SEQUENCE: 2
uuauugcuua agaauacgcg uag                                          23

<210> SEQ ID NO 3
<211> LENGTH: 22
<212> TYPE: RNA
<213> ORGANISM: Homo sapiens

<400> SEQUENCE: 3
auaaagcuag auaaccgaaa gu                                           22

<210> SEQ ID NO 4
<211> LENGTH: 23
<212> TYPE: RNA
<213> ORGANISM: Artificial sequence
```

```
<220> FEATURE:
<223> OTHER INFORMATION: miRNA 9 mimic

<400> SEQUENCE: 4
ucuuugguua ucuagcugua uga                                         23

<210> SEQ ID NO 5
<211> LENGTH: 40
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (5)..(10)
<223> OTHER INFORMATION: Xho1 restriction site

<400> SEQUENCE: 5
caccctcgag atgaagttat gggatgtcgt ggctgtctgc                       40

<210> SEQ ID NO 6
<211> LENGTH: 40
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (4)..(9)
<223> OTHER INFORMATION: Sal1 restriction site

<400> SEQUENCE: 6
aaagtcgaca tcagatacat ccacaccttt tagcggaatg                       40

<210> SEQ ID NO 7
<211> LENGTH: 39
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (19)..(24)
<223> OTHER INFORMATION: Xho1 restriction site

<400> SEQUENCE: 7
gacgccacca tggagagcct cgagagcggc ctgcccgcc                        39

<210> SEQ ID NO 8
<211> LENGTH: 39
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (16)..(21)
<223> OTHER INFORMATION: Xho1 restriction site

<400> SEQUENCE: 8
ggcgggcagg ccgctctcga ggctctccat ggtggcgtc                        39

<210> SEQ ID NO 9
<211> LENGTH: 531
<212> TYPE: DNA
<213> ORGANISM: Artificial sequence
<220> FEATURE:
<223> OTHER INFORMATION: Recombinant miR-124
```

<400> SEQUENCE: 9

```
gaacaaagag cctttggaag acgtcgctgt tatctcattg tctgtgtgat tgggggagct      60
gcggcgggga ggatgctgtg gtcccttcct ccggcgttcc ccaccccat ccctctcccc      120
gctgtcagtg cgcacgcaca cgcgccgctt tttatttctt tttcctggtt ttcttattcc     180
atcttctacc caccctctt cctttctttc acctttcctt ccttccttcc tcctttcctt     240
cctcaggaga aaggcctctc tctccgtgtt cacagcggac cttgatttaa atgtccatac     300
aattaaggca cgcggtgaat gccaagaatg gggctggctg agcaccgtgg gtcggcgagg    360
gcccgccaag gaaggagcga ccgaccgagc caggcgccct ccgcagacct ccgcgcagcg    420
gccgcgggcg cgaggggagg ggtctggagc tccctccggc tgcctgtccc gcaccggagc    480
ccgtggggtg gggaggtgtg cagcctgtga cagacagggg cttagagatg c             531
```

<210> SEQ ID NO 10
<211> LENGTH: 530
<212> TYPE: DNA
<213> ORGANISM: Artificial sequence
<220> FEATURE:
<223> OTHER INFORMATION: Recombinant miR-137

<400> SEQUENCE: 10

```
cagcactctt ctgtgttaag tatttgattt tgtgatttgt ctttcagaat tggaaataga     60
gcggccattt ggatttgggc aggaagcagc cgagcacagc tttggatcct tctttaggga    120
aatcgagtta tggatttatg gtcccggtca agctcagccc atccccaggc aggggcgggc    180
tcagcgagca gcaagagttc tggtggcggc ggcggcggca gtagcagcgg cagcggtagc    240
agcggcagcg gtagcagcgg cagcggcagc ttggtcctct gactctcttc ggtgacgggt    300
attcttgggt ggataatacg gattacgttg ttattgctta agaatacgcg tagtcgagga    360
gagtaccagc ggcaggggg cagcggccgc cctccccagc ccaccagctg gccactaaac     420
gcccgtggtt gccaaggtag cactttcttg ttcttttcat ttcctcgggt gttttcgcac    480
tggttccacc ggaaaggctg tgcgctgcgc ctctggtgac caggactgga                530
```

<210> SEQ ID NO 11
<211> LENGTH: 7544
<212> TYPE: DNA
<213> ORGANISM: Artificial sequence
<220> FEATURE:
<223> OTHER INFORMATION: CD-511_1 vector DNA

<400> SEQUENCE: 11

```
acgcgtgtag tcttatgcaa tactcttgta gtcttgcaac atggtaacga tgagttagca     60
acatgcctta caaggagaga aaagcaccg tgcatgccga ttggtggaag taaggtggta     120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg aaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcggggag    600
aattagatcg cgatgggaaa aaattcggtt aaggccaggg ggaaagaaaa aatataaatt    660
```

```
aaaacatata gtatgggcaa gcagggagct agaacgattc gcagttaatc ctggcctgtt      720
agaaacatca gaaggctgta gacaaatact gggacagcta caaccatccc ttcagacagg      780
atcagaagaa cttagatcat tatataatac agtagcaacc ctctattgtg tgcatcaaag      840
gatagagata aaagacacca aggaagcttt agacaagata gaggaagagc aaaacaaaag      900
taagaccacc gcacagcaag cggccactga tcttcagacc tggaggagga gatatgaggg      960
acaattggag aagtgaatta tataaatata aagtagtaaa aattgaacca ttaggagtag     1020
cacccaccaa ggcaaagaga agagtggtgc agagagaaaa aagagcagtg ggaataggag     1080 cttttgttcct tgggttcttg ggagcagcag gaagcactat gggcgcagcc tcaatgacgc     1140
tgacggtaca ggccagacaa ttattgtctg gtatagtgca gcagcagaac aatttgctga     1200
gggctattga ggcgcaacag catctgttgc aactcacagt ctggggcatc aagcagctcc     1260
aggcaagaat cctggctgtg gaaagatacc taaaggatca acagctcctg ggcatttggg     1320
gttgctctgg aaaactcatt tgcaccactg ctgtgccttg gaatgctagt tggagtaata     1380
aatctctgga acagattgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta cataacaaa     1560 ttggctgtgg tatataaaat tattcataat gatagtagga ggcttggtag gtttaagaat     1620 agttttttgct gtacttttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggttaacttt     1800
taaaagaaaa ggggggattg ggggtacag tgcaggggaa agaatagtag acataatagc     1860
aacagacata caaactaaag aattacaaaa acaaattaca aaaattcaaa attttatcga     1920
tactagtatt atgcccagta catgacctta tgggactttc ctacttggca gtacatctac     1980
gtattagtca tcgctattac catggtgatg cggttttggc agtacatcaa tgggcgtgga     2040
tagcggtttg actcacgggg atttccaagt ctccacccca ttgacgtcaa tgggagtttg     2100
ttttggcacc aaaatcaacg ggactttcca aatgtcgta acaactccgc cccattgacg     2160
caaatgggcg gtaggcgtgt acggtgggag gtctatataa gcagagctcg tttagtgaac     2220
cgtcagatcg cctggagacg ccatccacgc tgttttgacc tccatagaag attctagagc     2280
tagcgaattc gaatttaaat ggatccgcgg ccgcaaggat ctgcgatcgc tccggtgccc     2340
gtcagtgggc agagcgcaca tcgcccacag tccccgagaa gttgggggga gggtcggca     2400 attgaacggg tgcctagaga aggtggcgcg gggtaaactg ggaaagtgat gtcgtgtact     2460
ggctccgcct ttttcccgag ggtgggggag aaccgtatat aagtgcagta gtcgccgtga     2520
acgttctttt tcgcaacggg tttgccgcca gaacacagct gaagcttcga ggggctcgca     2580
tctctccttc acgcgcccgc cgccctacct gaggccgcca tccacgccgg ttgagtcgcg     2640
ttctgccgcc tcccgcctgt ggtgcctcct gaactgcgtc cgccgtctag gtaagtttaa     2700
agctcaggtc gagaccgggc ctttgtccgg cgctcccttg gagcctacct agactcagcc     2760
ggctctccac gctttgcctg acctgcttg ctcaactcta cgtctttgtt tcgttttctg     2820
ttctgcgccg ttacagatcc aagctgtgac cggcgcctac gctagacgcc accatggaga     2880
gcgacgagag cggcctgccc gccatggaga tcgagtgccg catcaccggc acctgaacg     2940 gcgtggagtt cgagctggtg gcggcggag agggcacccc caagcagggc cgcatgacca     3000
acaagatgaa gagcaccaaa ggcgcctga ccttcagccc ctacctgctg agccacgtga     3060
```

```
tgggctacgg cttctaccac ttcggcacct accccagcgg ctacgagaac cccttcctgc    3120
acgccatcaa caacggcggc tacaccaaca cccgcatcga aagtacgag acggcggcg      3180
tgctgcacgt gagcttcagc taccgctacg aggccggccg cgtgatcggc gacttcaagg    3240
tggtgggcac cggcttcccc gaggacacgc tgatcttcac cgacaagatc atccgcagca    3300
acgccaccgt ggagcacctg caccccatgg gcgataacgt gctggtgggc agcttcgccc    3360
gcaccttcag cctgcgcgac ggcggctact acagcttcgt ggtggacagc cacatgcact    3420
tcaagagcgc catccacccc agcatcctgc agaacggggg ccccatgttc gccttccgcc    3480
gcgtggagga gctgcacagc aacaccgagc tgggcatcgt ggagtaccag cacgccttca    3540
agaccccccat cgccttcgcc agatcccgcg ctcagtcgtc caattctgcc gtggacggca    3600
ccgccggacc cggctccacc ggatctcgct aagtcgacaa tcaacctctg gattacaaaa    3660
tttgtgaaag attgactggt attcttaact atgttgctcc ttttacgcta tgtggatacg    3720
ctgctttaat gcctttgtat catgctattg cttcccgtat ggctttcatt ttctcctcct    3780
tgtataaatc ctggttgctg tctctttatg aggagttgtg gcccgttgtc aggcaacgtg    3840
gcgtggtgtg cactgtgttt gctgacgcaa ccccccactgg ttggggcatt gccaccacct    3900
gtcagctcct ttccgggact ttcgctttcc cctcccctat gccacggcg gaactcatcg    3960
ccgcctgcct tgcccgctgc tggacagggg ctcggctgtt gggcactgac aattccgtgg    4020
tgttgtcggg gaaatcatcg tccttccctt ggctgctcgc ctgtgttgcc acctggattc    4080
tgcgcgggac gtccttctgc tacgtcccct cggccctcaa tccagcggac cttccttccc    4140
gcggcctgct gccggtctg cggcctcttc cgcgtcttcg ccttcgccct cagacgagtc    4200
ggatctccct ttgggccgcc tccccgcctg gtacctttaa gaccaatgac ttacaaggca    4260
gctgtagatc ttagccactt tttaaaagaa aaggggggac tggaagggct aattcactcc    4320
caacgaaaat aagatctgct ttttgcttgt actgggtctc tctggttaga ccagatctga    4380
gcctgggagc tctctggcta actagggaac ccactgctta agcctcaata aagcttgcct    4440
tgagtgcttc aagtagtgtg tgcccgtctg ttgtgtgact ctggtaacta gagatccctc    4500
agacccttt agtcagtgtg aaaatctct agcagtagta gttcatgtca tcttattatt      4560
cagtatttat aacttgcaaa gaaatgaata tcagagagtg agaggaactt gtttattgca    4620
gcttataatg gttacaaata aagcaatagc atcacaaatt tcacaaataa agcatttttt    4680
tcactgcatt ctagttgtgg tttgtccaaa ctcatcaatg tatcttatca tgtctggctc    4740
tagctatccc gcccctaact ccgcccagtt ccgcccattc tccgcccat ggctgactaa     4800
ttttttttat ttatgcagag gccgaggccg cctcggcctc tgagctattc cagaagtagt    4860
gaggaggctt ttttggaggc ctagactttt gcagagacgg cccaaattcg taatcatggt    4920
catagctgtt tcctgtgtga aattgttatc cgctcacaat tccacacaac atacgagccg    4980
gaagcataaa gtgtaaagcc tggggtgcct aatgagtgag ctaactcaca ttaattgcgt    5040
tgcgctcact gcccgctttc cagtcgggaa acctgtcgtg ccagctgcat taatgaatcg    5100
gccaacgcgc ggggagaggc ggtttgcgta ttgggcgctc ttccgcttcc tcgctcactg    5160
actcgctgcg ctcggtcgtt cggctgcggc gagcggtatc agctcactca aaggcggtaa    5220
tacggttatc cacagaatca ggggataacg caggaaagaa catgtgagca aaaggccagc    5280
aaaaggccag gaaccgtaaa aaggccgcgt tgctggcgtt tttccatagg ctccgccccc    5340
ctgacgagca tcacaaaaat cgacgctcaa gtcagaggtg gcgaaacccg acaggactat    5400
aaagatacca ggcgtttccc cctggaagct ccctcgtgcg ctctcctgtt ccgaccctgc    5460
```

```
cgcttaccgg atacctgtcc gcctttctcc cttcgggaag cgtggcgctt tctcatagct    5520
cacgctgtag gtatctcagt tcggtgtagg tcgttcgctc caagctgggc tgtgtgcacg    5580
aaccccccgt tcagcccgac cgctgcgcct tatccggtaa ctatcgtctt gagtccaacc    5640
cggtaagaca cgacttatcg ccactggcag cagccactgg taacaggatt agcagagcga    5700
ggtatgtagg cggtgctaca gagttcttga agtggtggcc taactacggc tacactagaa    5760
ggacagtatt tggtatctgc gctctgctga agccagttac cttcggaaaa agagttggta    5820
gctcttgatc cggcaaacaa accaccgctg gtagcggtgg ttttttttgtt tgcaagcagc    5880
agattacgcg cagaaaaaaa ggatctcaag aagatccttt gatcttttct acggggtctg    5940
acgctcagtg gaacgaaaac tcacgttaag ggattttggt catgagatta tcaaaaagga    6000
tcttcaccta gatcctttta aattaaaaat gaagttttaa atcaatctaa agtatatatg    6060
agtaaacttg gtctgacagt taccaatgct taatcagtga ggcacctatc tcagcgatct    6120
gtctatttcg ttcatccata gttgcctgac tccccgtcgt gtagataact acgatacggg    6180
agggcttacc atctggcccc agtgctgcaa tgataccgcg agacccacgc tcaccggctc    6240
cagatttatc agcaataaac cagccagccg gaagggccga gcgcagaagt ggtcctgcaa    6300
ctttatccgc ctccatccag tctattaatt gttgccggga agctagagta agtagttcgc    6360
cagttaatag tttgcgcaac gttgttgcca ttgctacagg catcgtggtg tcacgctcgt    6420
cgtttggtat ggcttcattc agctccggtt cccaacgatc aaggcgagtt acatgatccc    6480
ccatgttgtg caaaaaagcg gttagctcct tcggtcctcc gatcgttgtc agaagtaagt    6540
tggccgcagt gttatcactc atggttatgg cagcactgca taattctctt actgtcatgc    6600
catccgtaag atgcttttct gtgactggtg agtactcaac caagtcattc tgagaatagt    6660
gtatgcggcg accgagttgc tcttgcccgg cgtcaatacg ggataatacc gcgccacata    6720
gcagaacttt aaaagtgctc atcattggaa aacgttcttc ggggcgaaaa ctctcaagga    6780
tcttaccgct gttgagatcc agttcgatgt aacccactcg tgcacccaac tgatcttcag    6840
catcttttac tttcaccagc gtttctgggt gagcaaaaac aggaaggcaa aatgccgcaa    6900
aaaagggaat aagggcgaca cggaaatgtt gaatactcat actcttcctt tttcaatatt    6960
attgaagcat ttatcagggt tattgtctca tgagcggata catatttgaa tgtatttaga    7020
aaaataaaca aataggggtt ccgcgcacat ttccccgaaa agtgccacct gacgtctaag    7080
aaaccattat tatcatgaca ttaacctata aaaataggcg tatcacgagg ccctttcgtc    7140
tcgcgcgttt cggtgatgac ggtgaaaacc tctgacacat gcagctcccg gagacggtca    7200
cagcttgtct gtaagcggat gccgggagca gacaagcccg tcagggcgcg tcagcgggtg    7260
ttggcgggtg tcggggctgg cttaactatg cggcatcaga gcagattgta ctgagagtgc    7320
accatatgcg gtgtgaaata ccgcacagat gcgtaaggag aaaataccgc atcaggcgcc    7380
attcgccatt caggctgcgc aactgttggg aagggcgatc ggtgcgggcc tcttcgctat    7440
tacgccagct ggcgaaaggg ggatgtgctg caaggcgatt aagttgggta acgccagggt    7500
tttcccagtc acgacgttgt aaaacgacgg ccagtgccaa gctg                    7544
```

METHODS, SYSTEMS, AND COMPOSITIONS FOR NEURONAL DIFFERENTIATION OF MULTIPOTENT STROMAL CELLS

RELATED APPLICATIONS

This application is a National Phase of PCT Patent Application No. PCT/US2010/038168 having International filing date of Jun. 10, 2010, which claims the benefit of priority of U.S. Provisional Patent Application No. 61/185,773 filed on Jun. 10, 2009. The contents of the above applications are all incorporated herein by reference.

TECHNICAL FIELD

Without limitation, certain embodiments of the invention relate to induction and application of cell types for the treatment of mammalian nervous system injuries and diseases.

BACKGROUND

Certain nervous system injuries, autoimmune diseases affecting the central or peripheral nervous system, and neurodegenerative diseases are characterized by loss of specific cells, or abnormal functions of existing nerve cells, which cause the patient to present with different neurological signs and symptoms and potentially irreversible loss of neurological functions. As one example only, some patients suffering stroke, spinal cord injury, or other neural injury and degeneration experience loss of functioning cell types, or neurological conditions like Parkinson's disease and Alzheimer's disease which in turn results in loss of or abnormal function of system function. Currently therapeutic options for treating and restoring such cell and system functions are limited. Thus, a need remains for methods, systems, and compositions to promote additional therapies, including therapies addressed to replacement of missing or damaged nervous system cells, tissues, and functions.

BRIEF SUMMARY

Without limitation to only those embodiments described herein and without disclaimer, some embodiments of the invention comprise methods, systems, and compositions to selectively induce, whether in vitro or in vivo, the neuronal differentiation of multipotent stromal cells through the application of microRNAs, including but not limited to miRNA-124, miRNA-137 and/or miRNA-9* expression products of those miRNAs, and molecules and compositions containing functional elements of those miRNAs. Some embodiments of the invention also comprise the therapeutic administration and use of such induced cells to treat mammalian injuries and diseases, including but not limited to, nervous system injuries or diseases that may otherwise result in decreased cell or system function.

BRIEF DESCRIPTION OF THE DRAWINGS

Some embodiments of the present invention will now be described, by way of example only and without disclaimer of other embodiments, with reference to the accompanying drawings, in which:

DETAILED DESCRIPTION

Figure 1:
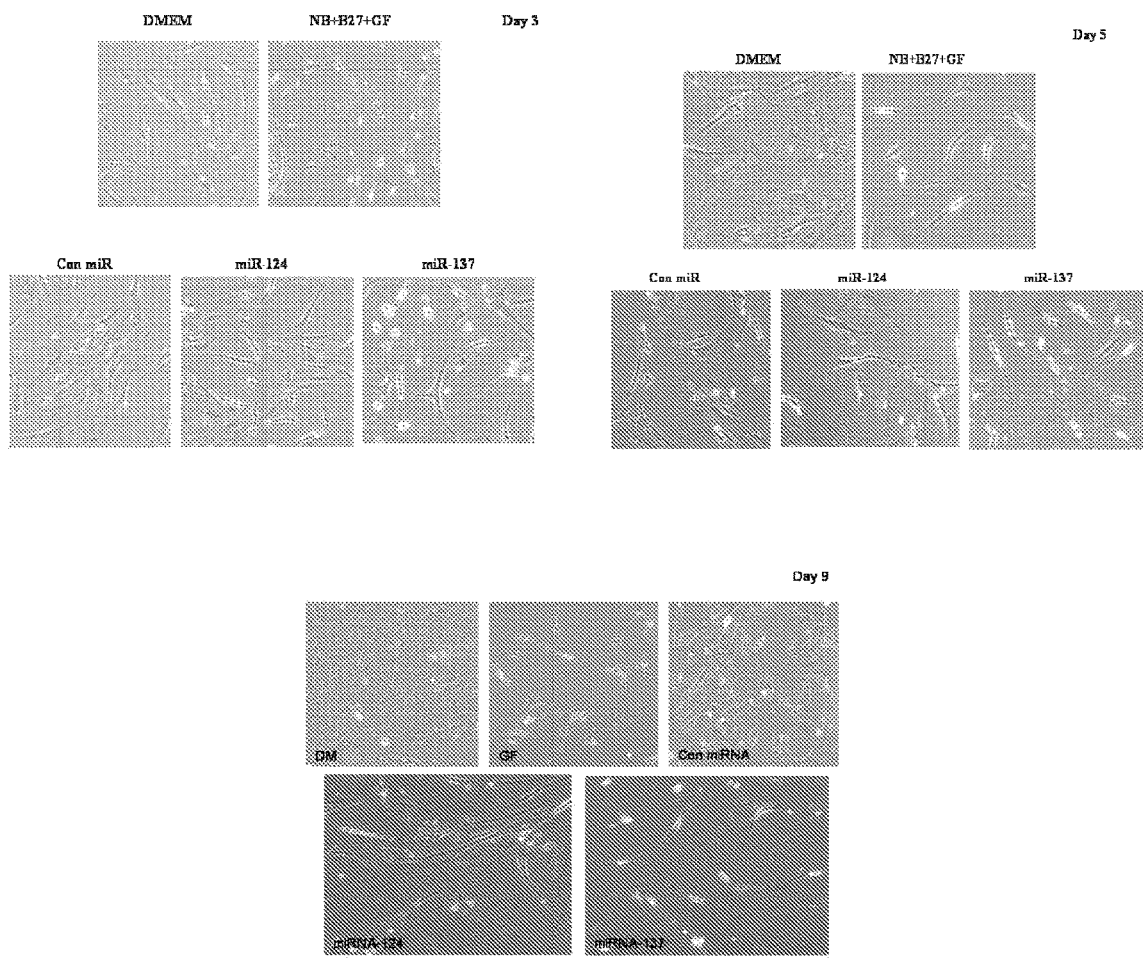
FIG. 1 shows bright field images of MSCs treated with growth factors or transfected with control miRNA and miRNA-124 or miRNA-137 for 3, 5 and 9 days.

Without limitation to only those embodiments expressly disclosed herein and without disclaiming any embodiments, some embodiments of the invention comprise methods, systems, and composition to selectively induce, whether in vitro or in vivo, the neuronal differentiation of multipotent stromal cells ("MSCs") through the application of microRNAs ("miRNA(s)" or "miR(s)"), including but not limited to, miRNA-124 and/or miRNA-137, and/or miRNA-9*, expression products of those miRNAs, and molecules and compositions containing functional elements of those miRNAs. Some embodiments of the invention also comprise the therapeutic administration and use of such induced cells to treat mammalian injuries and diseases, including but not limited to, nervous system injuries or diseases that may otherwise result in decreased cell or system function. In some embodiments, such induction of differentiated MSCs, and/or the resulting cells, may be used to treat cell, tissue, or organ damage in a patient by administering to said patient a therapeutically effective amount of an miRNA of interest, or of differentiated MSCs induced by such miRNAs.

We have discovered unexpectedly that certain miRNAs are capable of inducing long-term neuronal differentiation of MSCs for the use of cell-based therapies in subjects presenting with nervous system injury and disease, including but not limited to, neurodegenerative disorders and spinal injury. Such subjects may include mammals, including but not limited to, humans. Thus, we have discovered novel applications for such miRNAs and resulting induced MSCs which, among other possible uses, can reduce or alleviate the effects of certain nervous system injuries or diseases in mammals.

Without limitation, some embodiments of the invention comprise methods, systems, and/or compositions for inducing neuronal differentiation of MSCs through the use and expression of miRNA-124, miRNA-137, and/or miRNA-9*. MSCs are mesoderm-derived cells that typically reside in adult bone marrow, typically at very low concentration (about 1 in 10,000 nucleated cells). MSCs can differentiate to generate cells such as bone marrow stroma, blood vessels, fat, bone and cartilage. These cells may also have the potential to differentiate into neurons\ or glia-like cells depending on the environmental signals. Moreover, these cells may be further induced to express or maintained specific neuronal or glial phenotypes by incubation with different combinations of growth factors and hormones.

MSCs have been shown to exert therapeutic effects in a variety of neurological diseases and dysfunctions in experimental animal models and more recently in pilot clinical trials. Their effects have been mainly attributed to immunosuppressive and neuroprotective functions. In experimental autoimmune encephalitis ("EAE"), an animal model of multiple sclerosis ("MS"), treatment of mice with bone marrow derived MSCs resulted in significant suppression of disease manifestations. Some studies demonstrated that in addition to down regulation of autoimmunity neural differentiation of these cells increased their therapeutic effect in various instances such as the ischemic brain.

In our work, we tested the effect of three neuronal-associated miRNAs, miRNA-124, miRNA-137, and miRNA-9*, on the differentiation of human MSCs. These miRNAs are not normally expressed in MSCs. We discovered that the expression of miRNA-124, miRNA137, or miRNA-9* induced neuronal differentiation of MSCs, as indicated by the morphology of the cells and by the increased expression of βIII-tubulin and MAP2. miRNA-124, miRNA-137 and miRNA-9* induced an increase in tyrosine hydroxylase, suggesting differentiation of the MSCs to dopaminergic phenotype. One of the targets of pre-miRNA124 is the transcription factor REST that represses a large number of neuronal genes. Our results indicate that neuronal-associated miRNAs may induce long-term neuronal differentiation of MSCs for the use of cell-based therapy in neurodegenerative and neuroinflammatory disorders and spinal injury. One advantage of the use of miRNAs over the existing methods is that one can stably express pre-miRNAs in MSCs that will result in long-term neuronal differentiation, as compared with transient differentiation that is induced by treatment with growth factors. As such, easy access to patient's own bone marrow derived MSCs and the feasibility to enrich and expand MSCs in large numbers indicates that neuronal differentiation of such cells can serve as autologous neuronal stem cells that can be available for treatment of a large number of acquired or congenital neurological disorders associated with lack of or damaged neurons. As one example only without limitation, MSCs can be prepared from fat removed by liposuction and from cord blood or the placenta. Reduced immunogenicity of MSCs may facilitate the use of allogeneic neurons off the shelf or from matched or partially mismatched family member for treatment of conditions caused, as nonlimiting examples only, by congenital deficiencies of essential enzymes or other essential products.

Without limitation to only embodiments expressly disclosed herein, and without disclaiming any embodiments, some embodiments of the invention comprise:
1. the neuronal differentiation of MSCs through culture or other exposure to miRNAs, including but not limited to, miRNA124 and/or miRNA 137, and/or miRNA 9*.
2. transfection of MSCs with such miRNAs;
3. administration of MSCs induced in vitro into neuronal differentiation to a subject suffering from nervous system injury or disease; and/or
4. administration of MSCs transfected with such miRNAs to a subject suffering from nervous system injury or disease.

In some embodiments, without limitation, with reproducible transdifferentiation of MSCs to neurons, the therapeutic use of MSCs can be obtained and expanded, whether in vitro or in vivo, to include, as some examples only, treatment of cerebrovascular disease, spinal cord injury, treatment of neurodegenerative disorders such as amyotrophic lateral sclerosis ("ALS"), multiple sclerosis ("MS"), and related motor neuron diseases. Ongoing clinical studies already indicate that infusion of MSCs intrathecally and intravenously can improve partially the clinical manifestation of the disease in patients with MS and to a lesser extent in patients with ALS. Such clinical studies provide evidence that both intrathecal and intravenous infusions of MSCs are safe procedures since none of the treated patients has developed any severe side effect. Thus, cell therapy with MSCs represents prophetically an important approach for the treatment of a large number of neurological disorders, especially where MSCs can be induced into neurons or oligodendrocytes and/or secrete factors that can induce neurogenesis of locally residing stem cells.

EXAMPLES

The following examples of some embodiments of the invention are provided without limiting the invention to only those embodiments described herein and without disclaiming any embodiments.

microRNAs microRNAs ("miRNAs") represent a family of endogenous, small (as some nonlimited examples, 19-23 nucleotides) non-coding RNAs that function through the RNA interference ("RNAi") pathway to effect post-transcriptional gene silencing. miRNAs target the mRNAs of specific genes based on complementarity, and mediate either mRNA cleavage (perfect complementarity) or translation repression (partial complementarity). miRNAs have been demonstrated to play important roles in development and may function as fundamental genetic regulatory elements that serve to establish or maintain specific expression profiles determining cell fate.

Manipulating neuronal differentiation of MSCs may involve regulatory pathways that orchestrate the program of gene expression during the differentiation process. Differentiation often requires shifts in the mRNA and protein constitution of cells. One class of gene regulatory molecules are the microRNAs, a subclass of small RNAs, that are thought to use the elements of the RNA-interference pathway to post transcriptionally down-regulate the expression of protein-coding genes. miRNAs may play an important role in cell differentiation since they are predicted to individually regulate hundreds of target genes simultaneously.

Methods

To determine the effect of miRNA-124, miRNA-137, and miRNA-9* on the differentiation of MSCs, we employed three different preparations of these cells in passages 4-12. MSC cells were plated in DMEM+10% FCS for 24 hr and were then transfected with double-stranded RNA oligonucleotides of the mature sequence of the three miRNAs and with a negative control oligonucleotide. The miRNAs used were as follows:

Dharmacon Mimic Products:
MI0000443/MIMAT0000422—Human
Selected Precursor/Mature
Mature:
hsa-miR-124 [MIMAT0000422]
Precursor:
hsa-miR-124-1[MI0000443]
Organism:
Human
Mature Sequence:

(SEQ ID NO. 1)
UAAGGCACGCGGUGAAUGCC

MI0000454/MIMAT0000429—Human
Selected Precursor/Mature
Mature:
hsa-miR-137 [MIMAT0000429]
Precursor:
hsa-miR-137 [MI0000454]
Organism:
Human
Mature Sequence:

(SEQ ID NO. 2)
UUAUUGCUUAAGAAUACGCGUAG miRNA 9* Sequence:

```
                                            (SEQ ID NO. 3)
         AUAAAGCUAGAUAACCGAAAGU
``` miRNA 9 Mimic:

```
                                            (SEQ ID NO. 4)
         UCUUUGGUUAUCUAGCUGUAUGA
```

Following 3 days, cells were transferred to Neurobasal Medium (NB) supplemented with B27. Cell morphology was monitored every 24 hr and analysis of neuronal markers by either immunofluorescence staining, Western blot analysis or real-time PCR was performed following 5, 7 and 9 days post-transfection. As a positive control for the induction of neuronal differentiation, we used cells stimulated with combination of Shh, FGF8 and bFGF.

Results miRNA-124, miRNA-137, and miRNA-9* Promote Neuronal Differentiation of MSCs.

The pictures of FIG. 1 are representative of six separate experiments that gave similar results. As presented in FIG. 1, transfection of the cells with miRNA-137, miRNA-124 or miRNA-9* decreased cell proliferation and induced morphological differentiation in the cells already after 72 hr of transfection. Transfection of the MSCs with miRNA-137 induced rapid and robust morphological changes and the cells acquired a typical neuronal phenotype with compact cell bodies and elongated processes with varicosities. miRNA-124-transfected cells exhibited a strong decrease in cell proliferation followed by the generation of a number of cell types; elongated cells with long processes, small cells with multiple shorter processes and flat star-like cells. Cells transfected with the control miRNA resembled the control untreated cells. Interestingly, the effect of miRNA-137 was more rapid and stronger than that of the GF. About 90% of the miRNA-137 transfected cells exhibited neuronal morphology.

miRNA-124 miRNA-137 and miRNA-9* Increase the Expression of Neuronal Markers in MSCs.

Figure 2:
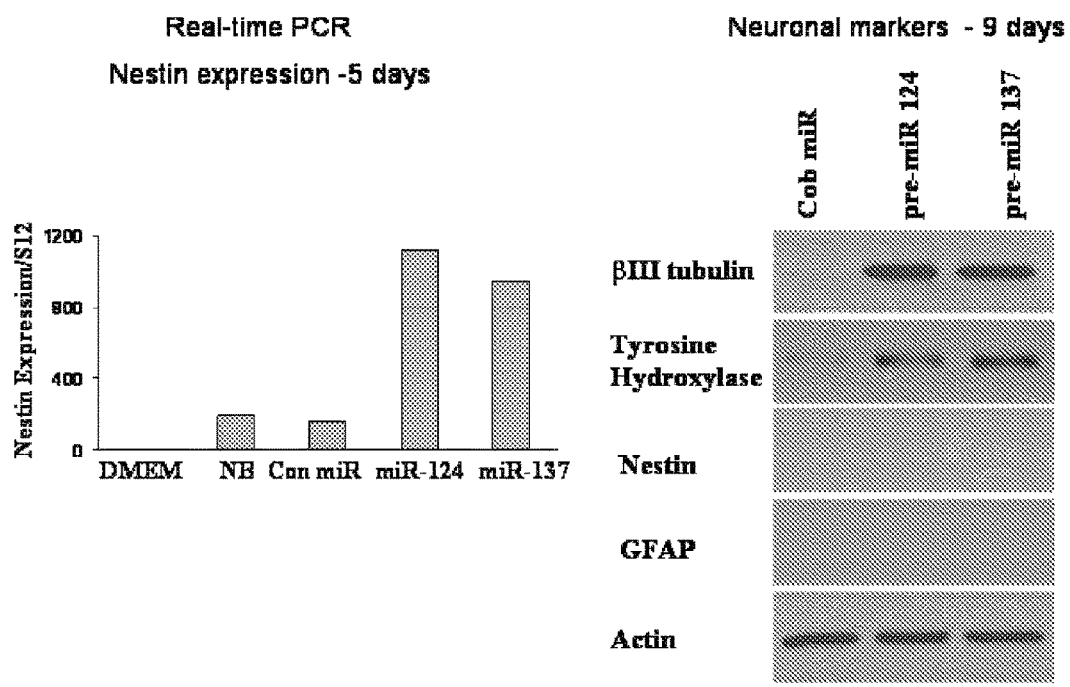
FIG. 2 is a data representation showing that miRNA-124, miRNA-137 and miRNA-9* induce neuronal markers in MSCs.

To further examine the effect of miRNA-124, miRNA-137 and miRNA-9* on neuronal differentiation, we examined the expression of the neural stem cell marker, nestin, the astrocytic marker GFAP and the neuronal markers beta III-tubulin and tyrosine hydroxylase. Cells were transfected with the appropriate miRNA or treated with DMEM or with neurobasal medium+B27. Following 5 days, the expression of nestin mRNA was determined using real-time PCR and the expression of nestin, GFAP, beta III-tubulin and tyrosine hydroxylase was examined after 9 days of treatment by Western blot analysis. The results represent five different experiments that gave similar results. FIG. 2 shows that after 5 days of transfection, there was a large increase in nestin mRNA as determined by real-time PCR. In contrast, after 9 days of transfection with the different miRNAs we found an increase in the expression of beta III-tubulin, whereas no expression of nestin or GFAP was observed. In addition we found that miRNA-137 and miRNA-9* induced a large increase in the expression of tyrosine hydroxylase, whereas a smaller increase was observed in miRNA-124 transfected cells. The expression of all these markers in the control miRNA transfected cells was absent or negligible.

miR-9* Induced the Dopaminergic Marker, Tyrosine Hydroxylase in MSCs.

Figure 3:
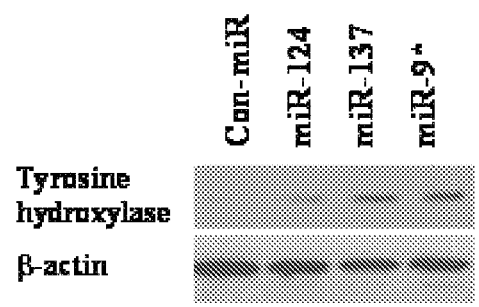
FIG. 3 shows Western Blot results following transfection of cells with tested miRNAs or treatment with DMEM.

FIG. 3 shows Western Blot results following MSC transfection with the appropriate miRNAs or treatment with DMEM. Following 9 days, the expression tyrosine hydroxylase was examined by Western blot analysis. The results represent five different experiments that gave similar results. miRNA-9* induced the dopaminergic marker, tyrosine hydroxylase, in MSCs.

Our results demonstrate that miRNA-124, miRNA-137 and miRNA-9* induce neuronal differentiation of MSCs, albeit to respectively different degrees in our test model. miRNA-137 induces a more rapid and robust effect resulting in a homogenous population of neuronal cells. The high level of tyrosine hydroxylase expressed in these cells suggests that these cells display a dopaminergic phenotype.

miRNA-124 also induces neuronal differentiation as determined by the high level of βIII-tubulin compared to the control miRNA-treated cells. In our work, this treatment resulted in a mixed population of cells which expressed lower level of tyrosine hydroxylase. None of the treatments induced astrocytic differentiation as determined by the lack of GFAP expression.

Moreover, following 5 days of treatment, both miRNAs induced a large transient increase in nestin expression, indicating generation of neural stem cell-like or neuronal progenitor-like cells. A controlled differentiation of MSCs to NSC or NPC-like cells may be further exploited to differentiate these cells to different neuronal lineages or to neurons with different phenotypes using specific transcription factors or specific combination of growth factors.

miRNA-124 and miRNA-9* have been reported to be involved in neuronal differentiation and neurite outgrowth. Similarly, there is one report demonstrating the effect of miRNA137 on neuronal differentiation of glioma stem cells and NSCs. However, no effects of miRNAs have been reported on the neuronal differentiation of MSCs and no effect of miRNA124 and miRNA137 has been shown on the generation of neurons with a specific phenotype. Moreover, none of these miRNAs has been reported to induce cells with a NSC/NPC phenotype.

miRNA-124 and miRNA-137 Induced Neuronal Differentiation in the Adipose and Cord Derived MSCs.

Figure 4:
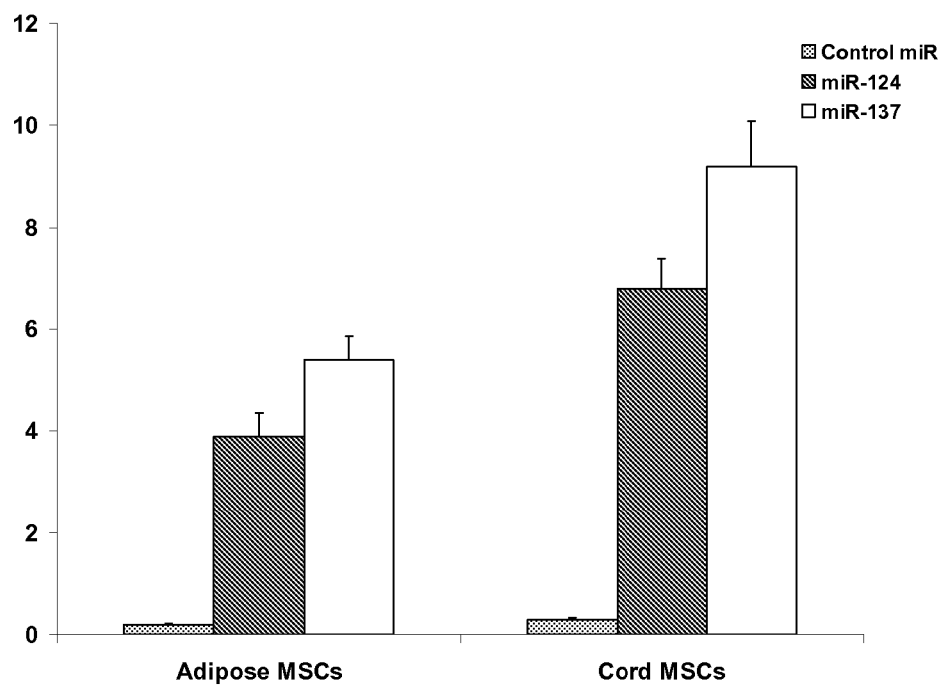
FIG. 4 shows results of transfecting adipose and cord derived MSCs with control miRNA, miRNA-124, or miRNA-137.

Adipose and cord derived MSCs were transfected with control miRNA, miRNA-124 and miRNA-137 similar to the bone marrow MSCs (FIG. 4).

Preparation of adipose-derived MSCs: Adipose-derived MSCs were obtained from liposuction from the thighs or abdominal walls. 100-200 ml aspirates were processed in a special designed Cytori separator that separates the MSCs from the fats cells and debris. The cells were further processed and maintained as described for the bone-marrow derived MSCs.

Preparation of human umbilical (cord) MSCs: Fresh human umbilical cords were obtained after birth (with parental consent) and collected in DMEM at 4° C. The umbilical cord vessels were removed and the mesenchymal tissue (Wharton's jelly) was minced into small pieces. Following centrifugation, at 250×g for 5 min the tissue was washed with serum-free DMEM was treated with collagenase at 37° C. for 18 h followed by digestion with 2.5% trypsin at 37° C. for 30 min. The dissociated MSCs were further dispersed and maintained in conditions similar to those described for bone marrow-derived MSCs.

After 12 days, mRNA was extracted and the levels of b3-tubulin and the house keeping gene S12 were determined using real-time PCR.

Our results (FIG. 4) demonstrate that miRNA-124 and miRNA-137 induce neuronal differentiation not only in bone-marrow derived MSCs but also in adipose-tissue and cord blood-derived cells. The neuronal marker beta III tubulin was induced in these cells following miRNA treatment. Each of these cell sources has its own advantages. Bone-marrow derived MSCs are very well characterized and have been used for over 20 years successfully with no oncogenic potential. Adipose-derived MSCs are less characterized but can be obtained in larger numbers and cord blood cells can be easily obtained in a non-invasive manner they do not require complete genetic compatibility between the donor and the patient and therefore are more accessible.

Construction of a Plasmid Containing Pre-miRNA and GDNF.

Since GDNF has been implicated in the survival of dopaminergic neurons, we constructed plasmids that co-express pre-miRNA-124 or pre-miRNA-137 together with GDNF under separate promoters.

Without limitation to only embodiments described herein, and without disclaiming any embodiments, steps for sequence and procedure of cloning the pre-miRNA GDNF vectors and that of the miRNAs are described with respect to step by step cloning of GDNF into premir vectors (CD-511_1 or PCDH-CMV-MCS-EF1-copGFP from System Biosciences).

cDNA of Homo sapiens glial cell derived neurotrophic factor ("GDNF") template was obtained from Origene. For cloning GDNF into premir 124 and 137 vectors (System Biosciences), primers with Xho1 and Sal1 restriction enzyme digestion sites for GDNF ORF were designed as follows:

Forward: cacc ctcgag(Xho1) atg aag tta tgg gat gtc gtg gct gtc tgc (SEQ ID NO. 5)

Reverse: aaa gtcgac(Sal1) tca gat aca tcc aca cct ttt agc gga atg (SEQ ID NO. 6)

After PCR, the GDNF DNA product was cleaned, then digested with Xho1 and Sal1, and the DNA was cleaned again, resulting in DNA of GDNF now ready for cloning.

Xho1 restriction site was added into the vector of premir 124 and premir 137 by using primers:

Forward: gac gcc acc atg gag agc ctc gag (Xho1) agc ggc ctg ccc gcc (SEQ ID NO. 7)

Reverse: ggc ggg cag gcc gct ctc gag (Xho1) gct ctc cat ggt ggc gtc (SEQ ID NO. 8)

The GFP gene was removed from premir 124 and 137 vector by using restriction enzymes Xho1 and Sal1, then the vector was cleaned.

Ligation of GDNF and premir 124 and 137 vectors. The ligated plasmids were transformed into One shot Top10 chemical competent cell. Plasmids with premir 124 and 137 were selected by culturing the clones, following by processing with mini prep.

The plasmids were digested by using Xho1 and Sal1 to detect the insert of GDNF. The plasmids were then sequenced. The sequence of miR-124 and 137 and the backbone of the premir vector:

MiR-124:
(SEQ ID NO. 9)

```
GAACAAAGAGCCTTTGGAAGACGTCGCTGTTATCTCATTGTCTGTGTGA
TTGGGGGAGCTGCGGCGGGGAGGATGCTGTGGTCCCTTCCTCCGGCGTT
CCCCACCCCCATCCCTCTCCCCGCTGTCAGTGCGCACGCACACGCGCCG
CTTTTTATTTCTTTTTCCTGGTTTTCTTATTCCATCTTCTACCCACCCC
TCTTCCTTTCTTTCACCTTTCCTTCCTTCCTTCCTCCTTTCCTTCCTCA
GGAGAAAGGCCTCTCTCTCCGTGTTCACAGCGGACCTTGATTTAAATGT
CCATACAATTAAGGCACGCGGTGAATGCCAAGAATGGGGCTGGCTGAGC
ACCGTGGGTCGGCGAGGGCCCGCCAAGGAAGGAGCGACCGACCGAGCCA
GGCGCCCTCCGCAGACCTCCGCGCAGCGGCCGCGGGCGCGAGGGGAGGG
GTCTGGAGCTCCCTCCGGCTGCCTGTCCCGCACCGGAGCCCGTGGGGTG
GGGAGGTGTGCAGCCTGTGACAGACAGGGGCTTAGAGATGC
```

MiR-137:
(SEQ ID NO. 10)

```
CAGCACTCTTCTGTGTTAAGTATTTGATTTTGTGATTTGTCTTTCAGAA
TTGGAAATAGAGCGGCCATTTGGATTTGGGCAGGAAGCAGCCGAGCACA
GCTTTGGATCCTTCTTTAGGGAAATCGAGTTATGGATTTATGGTCCCGG
TCAAGCTCAGCCCATCCCCAGGCAGGGGCGGGCTCAGCGAGCAGCAAGA
GTTCTGGTGGCGGCGGCGGCGGCAGTAGCAGCGGCAGCGGTAGCAGCGG
CAGCGGTAGCAGCGGCAGCGGCAGCTTGGTCCTCTGACTCTCTTCGGTG
ACGGGTATTCTTGGGTGGATAATACGGATTACGTTGTTATTGCTTAAGA
ATACGCGTAGTCGAGGAGAGTACCAGCGGCAGGGGGGCAGCGGCCGCCC
TCCCCAGCCCACCAGCTGGCCACTAAACGCCCGTGGTTGCCAAGGTAGC
ACTTTCTTGTTCTTTTCATTTCCTCGGGTGTTTTCGCACTGGTTCCACC
GGAAAGGCTGTGCGCTGCGCCTCTGGTGACCAGGACTGGA
```

The sequence of backbone vector (CD-511_1) was attached:

```
LOCUS CD511B_1_pCDH_CMV_ 7544 bp ds-DNA circular 16-
DEC-2008:
DEFINITION
ACCESSION
VERSION
SOURCE
  ORGANISM
COMMENT
COMMENT     ApEinfo:methylated:1
FEATURES Location/Qualifiers
 misc_feature 2315..2764
   /label=EF1 promoter
   /ApEinfo_fwdcolor=cyan
   /ApEinfo_revcolor=green
 misc_feature 2765..2789
   /label=EF1 promoter(1)
   /ApEinfo_label=EF1 promoter
   /ApEinfo_fwdcolor=cyan
   /ApEinfo_revcolor=green
 misc_feature 2874..3629
   /label=copGFP
   /ApEinfo_fwdcolor=#00ff00
   /ApEinfo_revcolor=green
```

-continued

```
misc_feature 3639..4229
 /label=WPRE
 /ApEinfo_fwdcolor=cyan
 /ApEinfo_revcolor=green
misc_feature 2790..2860
 /label=EF1 promoter(2)
 /ApEinfo_label=EF1 promoter
 /ApEinfo_fwdcolor=cyan
 /ApEinfo_revcolor=green
misc_feature 2765..2789
 /label=EFfwd primer
 /ApEinfo_fwdcolor=#ff80ff
 /ApEinfo_revcolor=green
misc_feature 1922..2183
 /label=CMV
 /ApEinfo_fwdcolor=#ff80ff
 /ApEinfo_revcolor=green
misc_feature 2272..2314
 /label=MCS
 /ApEinfo_fwdcolor=#80ff00
 /ApEinfo_revcolor=green
misc_feature 2205..2271
 /label=CMV(1)
 /ApEinfo_label=CMV
 /ApEinfo_fwdcolor=#ff80ff
 /ApEinfo_revcolor=green
misc_feature 2184..2204
 /label=DAB 90 primer forward
 /ApEinfo_fwdcolor=cyan
 /ApEinfo_revcolor=green
ORIGIN
                                                          (SEQ ID NO. 11)
   1 acgcgtgtag tcttatgcaa tactcttgta gtcttgcaac atggtaacga tgagttagca 61 acatgcctta caaggagaga aaaagcaccg tgcatgccga ttggtggaag taaggtggta 121 cgatcgtgcc ttattaggaa ggcaacagac gggtctgaca tggattggac gaaccactga 181 attgccgcat tgcagagata ttgtatttaa gtgcctagct cgatacaata aacgggtctc 241 tctggttaga ccagatctga gcctgggagc tctctggcta actagggaac ccactgctta 301 agcctcaata aagcttgcct tgagtgcttc aagtagtgtg tgcccgtctg ttgtgtgact 361 ctggtaacta gagatccctc agaccctttt agtcagtgtg gaaaatctct agcagtggcg 421 cccgaacagg gacctgaaag cgaaagggaa accagagctc tctcgacgca ggactcggct 481 tgctgaagcg cgcacggcaa gaggcgaggg gcggcgactg gtgagtacgc caaaaatttt 541 gactagcgga ggctagaagg agagagatgg gtgcgagagc gtcagtatta gcgggggag 601 aattagatcg cgatgggaaa aaattcggtt aaggccaggg ggaaagaaaa aatataaatt 661 aaaacatata gtatgggcaa gcagggagct agaacgattc gcagttaatc ctggcctgtt 721 agaaacatca gaaggctgta gacaaatact gggacagcta caaccatccc ttcagacagg 781 atcagaagaa cttagatcat tatataatac agtagcaacc ctctattgtg tgcatcaaag 841 gatagagata aaagacacca aggaagcttt agacaagata gaggaagagc aaaacaaaag 901 taagaccacc gcacagcaag cggccactga tcttcagacc tggaggagga gatatgaggg 961 acaattggag aagtgaatta tataaatata agtagtaaa aattgaacca ttaggagtag 1021 cacccaccaa ggcaaagaga agagtggtgc agagagaaaa aagagcagtg gaataggag 1081 ctttgttcct tgggttcttg ggagcagcag gaagcactat gggcgcagcc tcaatgacgc 1141 tgacggtaca ggccagacaa ttattgtctg gtatagtgca gcagcagaac aatttgctga 1201 gggctattga ggcgcaacag catctgttgc aactcacagt ctggggcatc aagcagctcc 1261 aggcaagaat cctggctgtg gaaagatacc taaggatca acagctcctg ggatttggg 1321 gttgctctgg aaaactcatt tgcaccactg ctgtgccttg gaatgctagt tggagtaata 1381 aatctctgga acagattgga atcacacgac ctggatggag tgggacagag aaattaacaa 1441 ttacacaagc ttaatacact ccttaattga agaatcgcaa aaccagcaag aaaagaatga
```

-continued

```
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggttaacttt
1801 taaaagaaaa gggggattg gggggtacag tgcagggaa agaatagtag acataatagc
1861 aacagacata caaactaaag aattacaaaa acaaattaca aaaattcaaa attttatcga
1921 tactagtatt atgcccagta catgacctta tgggactttc ctacttggca gtacatctac
1981 gtattagtca tcgctattac catggtgatg cggttttggc agtacatcaa tgggcgtgga
2041 tagcggttg actcacgggg atttccaagt ctccacccca ttgacgtcaa tgggagtttg
2101 ttttggcacc aaaatcaacg ggactttcca aaatgtcgta acaactccgc cccattgacg
2161 caaatgggcg gtaggcgtgt acggtgggag gtctatataa gcagagctcg tttagtgaac
2221 cgtcagatcg cctggagacg ccatccacgc tgttttgacc tccatagaag attctagagc
2281 tagcgaattc gaatttaaat ggatccgcgg ccgcaaggat ctgcgatcgc tccggtgccc
2341 gtcagtgggc agagcgcaca tcgcccacag tccccgagaa gttgggggga gggtcggca
2401 attgaacggg tgcctagaga aggtggcgcg gggtaaactg ggaaagtgat gtcgtgtact
2461 ggctccgcct ttttcccgag ggtgggggag aaccgtatat aagtgcagta gtcgccgtga
2521 acgttctttt tcgcaacggg tttgccgcca gaacacagct gaagcttcga ggggctcgca
2581 tctctccttc acgcgcccgc cgcccctacct gaggccgcca tccacgccgg ttgagtcgcg
2641 ttctgccgcc tcccgcctgt ggtgcctcct gaactgcgtc cgccgtctag gtaagtttaa
2701 agctcaggtc gagaccgggc ctttgtccgg cgctcccttg gagcctacct agactcagcc
2761 ggctctccac gctttgcctg accctgcttg ctcaactcta cgtctttgtt tcgttttctg
2821 ttctgcgccg ttacagatcc aagctgtgac cggcgcctac gctagacgcc accatggaga
2881 gcgacgagag cggcctgccc gccatggaga tcgagtgccg catcaccggc accctgaacg
2941 gcgtggagtt cgagctggtg ggcggcggag agggcacccc caagcagggc gcatgacca
3001 acaagatgaa gagcaccaaa ggcgccctga ccttcagccc ctacctgctg agccacgtga
3061 tgggctacgg cttctaccac ttcggcacct accccagcgg ctacgagaac cccttcctgc
3121 acgccatcaa caacggcggc tacaccaaca cccgcatcga gaagtacgag gacggcggcg
3181 tgctgcacgt gagcttcagc taccgctacg aggccggccg cgtgatcggc gacttcaagg
3241 tggtgggcac cggcttcccc gaggacagcg tgatcttcac cgacaagatc atccgcagca
3301 acgccaccgt ggagcacctg caccccatgg gcgataacgt gctggtgggc agcttcgccc
3361 gcaccttcag cctgcgcgac ggcggctact acagcttcgt ggtggacagc cacatgcact
3421 tcaagagcgc catccacccc agcatcctgc agaacggggg ccccatgttc gccttccgcc
3481 gcgtggagga gctgcacagc aacaccgagc tgggcatcgt ggagtaccag cacgccttca
3541 agacccccat cgccttcgcc agatcccgcg ctcagtcgtc caattctgcc gtggacggca
3601 ccgccggacc cggctccacc ggatctcgct aagtcgacaa tcaacctctg gattacaaaa
3661 tttgtgaaag attgactggt attcttaact atgttgctcc ttttacgcta tgtggatacg
3721 ctgctttaat gcctttgtat catgctattg cttcccgtat ggctttcatt ttctcctcct
3781 tgtataaatc ctggttgctg tctctttatg aggagttgtg gcccgttgtc aggcaacgtg
3841 gcgtggtgtg cactgtgttt gctgacgcaa cccccactgg ttggggcatt gccaccacct
3901 gtcagctcct ttccgggact ttcgctttcc ccctccctat tgccacggcg gaactcatcg
```

-continued

```
3961 ccgcctgcct tgcccgctgc tggacagggg ctcggctgtt gggcactgac aattccgtgg 4021 tgttgtcggg gaaatcatcg tcctttcctt ggctgctcgc ctgtgttgcc acctggattc 4081 tgcgcgggac gtccttctgc tacgtccctt cggccctcaa tccagcggac cttccttccc 4141 gcggcctgct gccggctctg cggcctcttc cgcgtcttcg ccttcgccct cagacgagtc 4201 ggatctccct ttgggccgcc tccccgcctg gtacctttaa gaccaatgac ttacaaggca 4261 gctgtagatc ttagccactt tttaaaagaa aaggggggac tggaagggct aattcactcc 4321 caacgaaaat aagatctgct ttttgcttgt actgggtctc tctggttaga ccagatctga 4381 gcctgggagc tctctggcta actagggaac ccactgctta agcctcaata agcttgcct 4441 tgagtgcttc aagtagtgtg tgcccgtctg ttgtgtgact ctggtaacta gagatccctc 4501 agacccttt agtcagtgtg gaaaatctct agcagtagta gttcatgtca tcttattatt 4561 cagtatttat aacttgcaaa gaaatgaata tcagagagtg agggaactt gtttattgca 4621 gcttataatg gttacaaata aagcaatagc atcacaaatt tcacaaataa agcattttt 4681 tcactgcatt ctagttgtgg tttgtccaaa ctcatcaatg tatcttatca tgtctggctc 4741 tagctatccc gcccctaact ccgcccagtt ccgcccattc tccgccccat ggctgactaa 4801 ttttttttat ttatgcagag gccgaggccg cctcggcctc tgagctattc cagaagtagt 4861 gaggaggctt ttttggaggc ctagacttt gcagagacgg cccaaattcg taatcatggt 4921 catagctgtt tcctgtgtga aattgttatc cgctcacaat tccacacaac atacgagccg 4981 gaagcataaa gtgtaaagcc tggggtgcct aatgagtgag ctaactcaca ttaattgcgt 5041 tgcgctcact gcccgctttc cagtcgggaa acctgtcgtg ccagctgcat taatgaatcg 5101 gccaacgcgc ggggagaggc ggtttgcgta ttgggcgctc ttccgcttcc tcgctcactg 5161 actcgctgcg ctcggtcgtt cggctgcggc gagcggtatc agctcactca aaggcggtaa 5221 tacggttatc cacagaatca ggggataacg caggaaagaa catgtgagca aaaggccagc 5281 aaaaggccag gaaccgtaaa aaggccgcgt tgctggcgtt tttccatagg ctccgccccc 5341 ctgacgagca tcacaaaaat cgacgctcaa gtcagaggtg gcgaaacccg acaggactat 5401 aaagatacca ggcgtttccc cctggaagct ccctcgtgcg ctctcctgtt ccgaccctgc 5461 cgcttaccgg atacctgtcc gcctttctcc cttcgggaag cgtggcgctt tctcatagct 5521 cacgctgtag gtatctcagt tcggtgtagg tcgttcgctc caagctgggc tgtgtgcacg 5581 aaccccccgt tcagcccgac cgctgcgcct tatccggtaa ctatcgtctt gagtccaacc 5641 cggtaagaca cgacttatcg ccactggcag cagccactgg taacaggatt agcagagcga 5701 ggtatgtagg cggtgctaca gagttcttga agtggtggcc taactacggc tacactagaa 5761 ggacagtatt tggtatctgc gctctgctga gccagttac cttcggaaaa agagttggta 5821 gctcttgatc cggcaaacaa accaccgctg gtagcggtgg ttttttttgtt tgcaagcagc 5881 agattacgcg cagaaaaaaa ggatctcaag aagatccttt gatcttttct acgggtctg 5941 acgctcagtg gaacgaaaac tcacgttaag ggattttggt catgagatta tcaaaaagga 6001 tcttcaccta gatccttta aattaaaaat gaagttttaa atcaatctaa agtatatatg 6061 agtaaacttg gtctgacagt taccaatgct taatcagtga ggcacctatc tcagcgatct 6121 gtctatttcg ttcatccata gttgcctgac tccccgtcgt gtagataact acgatacggg 6181 agggcttacc atctggcccc agtgctgcaa tgataccgcg agacccacgc tcaccggctc 6241 cagatttatc agcaataaac cagccagccg aagggccga gcgcagaagt ggtcctgcaa 6301 ctttatccgc ctccatccag tctattaatt gttgccggga agctagagta agtagttcgc 6361 cagttaatag tttgcgcaac gttgttgcca ttgctacagg catcgtggtg tcacgctcgt
```

```
-continued
6421 cgtttggtat ggcttcattc agctccggtt cccaacgatc aaggcgagtt acatgatccc 6481 ccatgttgtg caaaaaagcg gttagctcct tcggtcctcc gatcgttgtc agaagtaagt 6541 tggccgcagt gttatcactc atggttatgg cagcactgca taattctctt actgtcatgc 6601 catccgtaag atgcttttct gtgactggtg agtactcaac caagtcattc tgagaatagt 6661 gtatgcggcg accgagttgc tcttgcccgg cgtcaatacg ggataatacc gcgccacata 6721 gcagaacttt aaaagtgctc atcattggaa aacgttcttc ggggcgaaaa ctctcaagga 6781 tcttaccgct gttgagatcc agttcgatgt aacccactcg tgcacccaac tgatcttcag 6841 catctttac tttcaccagc gtttctgggt gagcaaaaac aggaaggcaa aatgccgcaa 6901 aaaagggaat aagggcgaca cggaaatgtt gaatactcat actcttcctt tttcaatatt 6961 attgaagcat ttatcagggt tattgtctca tgagcggata catatttgaa tgtatttaga 7021 aaaataaaca aataggggtt ccgcgcacat ttccccgaaa agtgccacct gacgtctaag 7081 aaaccattat tatcatgaca ttaacctata aaaataggcg tatcacgagg cccttcgtc 7141 tcgcgcgttt cggtgatgac ggtgaaaacc tctgacacat gcagctccg gagacggtca 7201 cagcttgtct gtaagcggat gccgggagca gacaagcccg tcagggcgcg tcagcgggtg 7261 ttggcgggtg tcggggctgg cttaactatg cggcatcaga gcagattgta ctgagagtgc 7321 accatatgcg gtgtgaaata ccgcacagat gcgtaaggag aaaataccgc atcaggcgcc 7381 attcgccatt caggctgcgc aactgttggg aagggcgatc ggtgcgggcc tcttcgctat 7441 tacgccagct ggcgaaaggg ggatgtgctg caaggcgatt aagttgggta acgccagggt 7501 tttcccagtc acgacgttgt aaaacgacgg ccagtgccaa gctg
```

We found that MSCs transfected with these plasmids secrete GDNF and express the respective miRNAs. Thus, the GDNF secreted by the differentiated dopaminergic neurons is expected to provide survival signals to the differentiated cells and to endogenous dopaminergic neurons.

Construction of Inducible miRNAs.

Implanted MSCs have been reported to migrate to damaged tissues in the central nervous systems and to exert neurotrophic and immunomodulatory effects. Specifically, in Parkinson's animal models, implanted MSCs have been shown to engraft in the lesioned striatum. In some embodiments, without limitation, inducible pre-miRNA expression vectors might be used that will allow the induction of the specific pre-miRNA expression at desired time points. Thus, MSCs would be transfected with the specific pre-miRNA and its expression would be induced at different time points prior or following the engraftment of the MSCs in the lesioned striatum. For such studies we have employed the inducible miRNA and living color, fluorescent protein reporters using the Tet-on system (Clontech). This system allows the induction of the specific miRNA by the addition of a promoter, as one example, only, by doxycyline, and the identification of cells in which the miRNA is produced.

In summary, we have demonstrated the ability of miRNA124, miRNA137 and miRNA-9* to induce transdifferentiation of MSCs to NSC/NPC and neurons with a specific neuronal phenotype (miRNA137). Additional neuronal miRNAs such as miRNA-9 and miR218 may also effect transdifferentiation of MSCs and induce neuronal differentiation.

An advantage of using miRNAs over the existing methods is that one can stably express pre-miRNAs in the MSCs which will result in long-term neuronal differentiation as compared with transient differentiation that is induced by treatment with growth factors.

Our work indicates that neuronal-associated miRNAs may be employed to induce long-term neuronal differentiation of MSCs for the use of cell-based therapy in neurodegenerative disorders and spinal injury, as some examples only, as shown by:

1. Neuronal differentiation of MSCs by microRNAs (miRNA-124, miRNA-137, miRNA-9*);
2. Specific dopaminergic differentiation of MSCs by miRNA-137, miRNA-124 and miRNA-9*; and
3. Induction by microRNAs of transient differentiation of MSCs to neural stem cell like- or neural progenitor-like cells. Transfection with the miRNAs provides a window of opportunity where cells can be differentiated to the different lineages of the central nervous system (neurons, astrocytes and oligodendrocytes) or to a specific neuronal phenotype using transcription factors or a specific combination of growth factors. This window can be controlled by level of miRNA expression or by a specific time point post-transfection.

The ability of miRNAs to transdifferentiate MSCs to uncommitted progenitor cells and to different neuronal cell subsets makes it possible to use these cells for treatment of a large variety of neurological diseases, including spinal cord and peripheral nerve injuries, damage to the central nervous system caused by hemorrhage or obstructive lesions ("CVA") or to traumatic central or peripheral nerve injury. In addition, transdifferentiated MSCs may be employed in the case of neurodegenerative diseases caused by idiopathic autoimmune diseases ("EAE") or diseases such as Parkinson's disease or Alzheimer/s disease or diseases with unknown etiology such as ALS. Moreover, improvement of neurological functions by transdifferentiated MSCs may also be used in various degenerative disorders caused by drug-induced neuronal damage and/or toxicity.

Thus, in our work, miRNA-124, miRNA-137 and miRNA-9* promote neural differentiation of MSC's, with accompanying morphological changes and expression of phenotypic markers.

The inducing miRNA(s) of some embodiments would be administered and dosed in accordance with good medical practice, taking into account the techniques of use to accomplish the desired effect of target MSCs, the clinical condition of the individual patient, the site and method of administration, scheduling of administration, patient age, sex, body weight and other factors known to medical practitioners. The "pharmaceutically effective amount" for purposes herein is thus determined by such considerations as are known in the art. The amount must be effective to achieve improvement, including but not limited to, the desired differentiation of MSCs in vivo and/or in vitro, decreased damage or injury, or improvement or elimination of symptoms and other indicators as are selected as appropriate measures by those skilled in the art.

Embodiments of the invention may expand the therapeutic window for treatment of nervous system injury and diseases and could be applied to treatment of a large patient population which suffers such injury and diseases each year in the United States. Thus, in some embodiments, the invention comprises novel methods to prevent, control, or alleviate mammalian nervous system injury and disease, including without limitation, brain damage, neural degeneration, or spinal cord injury, through the selective application of inducing miRNAs comprising embodiments of the invention. In accordance with some embodiments, without limitation, one may effect such therapeutic intervention through the use and/or administration of one or more such miRNAs to induce differentiation in target cells in vivo or in vitro for use in treatment to limit the effects of such injury or disease. Thus, without limitation and without disclaimer of subject matter, some embodiments comprise novel compositions and methods to prevent, control, or alleviate mammalian injury, including without limitation, brain damage, through the selective application and/or induction of trans-differentiated MSCs.

This application may reference various publications by author, citation, and/or by patent number, including without limitation, articles, presentations, and United States patents. The disclosures of each of any such references in their entireties are hereby incorporated by reference into this application.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

What is claimed is:

1. A method of trans-differentiating mammalian multipotent stromal cells into neuronal stem cells, the method comprising the steps of:

a) providing a population of mammalian multipotent stromal cells; and b) expressing microRNA-137 in the population of mammalian multipotent stromal cells so as to generate a population of neuronal stem cells expressing nestin, thereby trans-differentiating mammalian multipotent stromal cells into neuronal stem cells.

2. The method of claim 1, wherein the mammal is a human.

3. The method of claim 1, further comprising step (c) comprising analyzing a marker in said population of neuronal stem cells, wherein said marker comprises a neuronal morphology.

4. The method of claim 1, wherein said mammalian multipotent stromal cells are derived from a tissue selected from the group consisting of adipose tissue, umbilical cord tissue, bone marrow tissue and placenta tissue.

5. The method of claim 1, further comprising expressing in said mammalian multipotent stromal cells glial derived neurotrophic factor (GDNF).

6. The method of claim 1, wherein said expressing comprises transfection, overexpression of exogenous miRNA or transduction of pre-miRNA.

\* \* \* \* \*